United States Patent [19]

Frenken

[11] Patent Number: 4,472,516
[45] Date of Patent: Sep. 18, 1984

[54] PROCESS FOR DEACTIVATING CATALYTICALLY ACTIVE SITES ON THE EXTERNAL SURFACE OF CRYSTALLINE SILICATE CATALYSTS, AS WELL AS CRYSTALLINE SILICATE CATALYSTS THE CATALYTIC PROPERTIES OF THE EXTERNAL SURFACE OF WHICH DIFFER FROM THOSE OF THE PORE SURFACE

[75] Inventor: Petrus M. G. Frenken, Thorn, Netherlands

[73] Assignee: Stamicarbon B.V., Geleen, Netherlands

[21] Appl. No.: 467,214

[22] Filed: Feb. 17, 1983

[30] Foreign Application Priority Data

Feb. 17, 1982 [NL] Netherlands ......................... 82 00615

[51] Int. Cl.³ .......................... B01J 29/06; B01J 21/02
[52] U.S. Cl. ...................................... 502/60; 502/232; 502/263
[58] Field of Search ............................. 252/432, 455 Z

[56] References Cited

U.S. PATENT DOCUMENTS 3,702,886 11/1972 Argauer et al. ..................... 423/328
3,806,466 4/1974 Bird et al. .......................... 502/185
4,002,697 1/1977 Chen .................................. 585/454
4,100,215 7/1978 Chen .................................. 585/454
4,231,899 11/1980 Chen et al. ....................... 252/455 Z
4,254,297 3/1981 Frenken et al. ..................... 585/640

Primary Examiner—Delbert E. Gantz
Assistant Examiner—William G. Wright
Attorney, Agent, or Firm—Cushman, Darby & Cushman

[57] ABSTRACT

Disclosed is a method for selectively deactivating catalytically active sites which occur only on the surface of a zeolite of boralite catalyst. Active sites occurring on the interior of the pores are masked by saturating the catalyst with an organic compound which fills substantially the whole of the catalyst pore volume. The catalyst so treated is then exposed to a deactivating agent, such as a solution of an alkali metal salt which is substantially immiscible with, substantially insoluble in, and which is otherwise unreactive to said pore-filling compound. The catalyst is then treated to drive off the pore-filling compound, yielding a catalyst selectively deactivated only on the external surface, but which is not deactivated within the pores. The treatment enables the catalyst to be used for e.g. hydrocarbon conversion for long time periods without carbon buildups around the pore entrances, which buildup would otherwise either restrict entry into the pores by reactants or exit therefrom by product.

9 Claims, 3 Drawing Figures

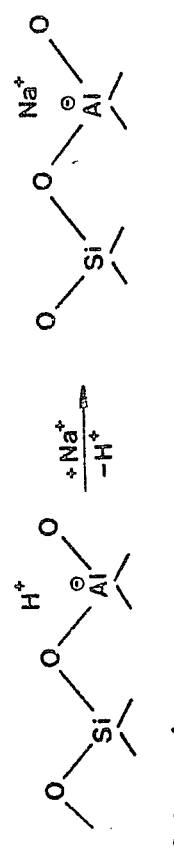
Scheme 1
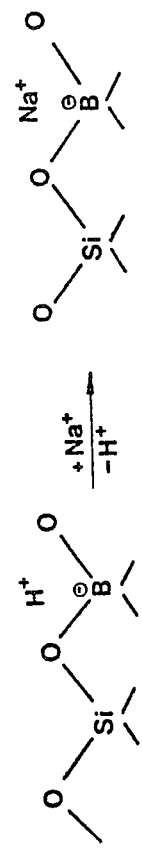
Scheme 2
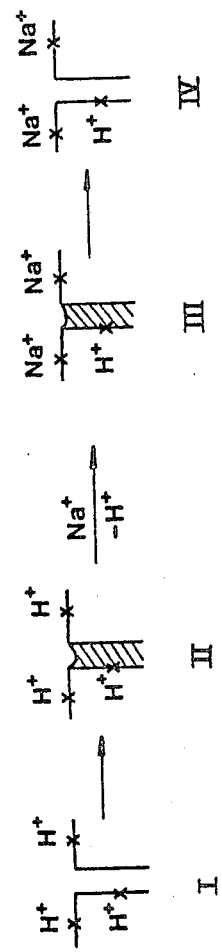
Scheme 3

PROCESS FOR DEACTIVATING CATALYTICALLY ACTIVE SITES ON THE EXTERNAL SURFACE OF CRYSTALLINE SILICATE CATALYSTS, AS WELL AS CRYSTALLINE SILICATE CATALYSTS THE CATALYTIC PROPERTIES OF THE EXTERNAL SURFACE OF WHICH DIFFER FROM THOSE OF THE PORE SURFACE

FIELD OF THE INVENTION

This invention relates to a process for deactivating catalytically active sites on the external surface of porous crystalline aluminosilicate and/or borosilicate catalysts.

BACKGROUND OF THE INVENTION

Aluminosilicates and borosilicates constitute crystalline modifications of silicon dioxide wherein silicon atoms have been replaced by aluminium or boron atoms, respectively. The Si/Al and Si/B ratios of these porous materials may vary within very wide limits but, for use as a catalyst, the Si/Al ratio in an aluminosilicate catalyst generally ranges between about 6 and about 2000, while the Si/B ratio in a borosilicate catalyst generally ranges between about 3 and about 2000. Hereinafter the terms "aluminosilicate" and "borosilicate" will be denoted by the terms "zeolite" and "boralite", respectively.

Zeolites are generally known from the literature, U.S. Pat. No. 3,702,886 being pointed out in particular and herein incorporated by reference. Boralites have likewise been described, for example in U.S. Pat. Nos. 4,269,813 and 4,254,297 both of which are also incorporated by reference.

Silicon atoms in boralites and zeolites can be replaced by germanium atoms. Minor quantities of the silicon and/or germanium can in turn be replaced by other elements such as iron, chromium, vanadium, molybdenum, arsenic, manganese, or gallium.

Zeolites and boralites are characterized by their crystal structure, which is, in turn, an essential factor in the structure of their internal pore system. The internal pore system plays a large part in the catalytic properties of these materials.

Catalytic active sites will however not only occur in the internal pores of the material, but also on the external surface of the silicate crystallites. It should be emphasized that in this context as well as throughout this specification the expression 'pore' is ment to refer to the structural, internal, pore system of the silicate materials involved, whereas the expression 'surface' or 'external surface' of the catalyst materials and/or crystallites is ment to refer to that surface of the materials which is not within said structural, internal pores.

As there exist catalytically active sites on the external surface of the silicate cristallites, there will also occur, of course, active sites near the entrances to the pores. Consequently, when these silicates are used as catalysts in a process such as hydrocarbon conversion, carbon will build up at the pore entrances and result in the pores closing off completely, or becoming less and less accessible as time passes to the entry of reactants into, or the exit of products out of, the pores. The catalytic activity of the zeolite or boralite accordingly decreases and the carbon buildup must be removed. The removal is laborious and expensive, in addition to which the yield of product decreases strongly as the buildup at the pore entrances progresses.

Known processes exist which have dealt with this problem in various fashions. For example, from the DD Pat. No. 111 091 it is known to block the active sites on the external surfaces of zeolite catalysts with alkaline compounds the molecular size of which exceeds that of the pores of the zeolite.

From U.S. Pat. No. 3,404,192 it is known to poison the external surface of zeolite catalysts with substances not capable of penetrating into the pores of the zeolite.

From U.S. Pat. No. 4,273,753 it is known to treat zeolites with dealuminating agents containing halogen. If the molecular size of the dealuminating agent is greater than the pore openings, substantially only the external surfaces of the zeolites will be dealuminated.

The disadvantage of these known processes is that the deactivating agent has to be very specific in view of the pore system of the material to be superficially, deactivated. In particular it is necessary, in order to avoid the partial deactivation of the pores themselves, there must be a substantial difference in size between the molecules of the reagents used for deactivating the external surface and the openings of the pores. The use of such very specific deactivating agents is not only detrimental to the universatillity of the method but also to the economy, and simplicity of use of the method. The further disadvantage of these known processes lies in the fact that they are limited to the treatment of catalysts having relatively small pores.

SUMMARY OF THE INVENTION

The object of the invention is to provide a more universal and efficient process for deactivating at least part of the catalytically active sites occurring on the external surface of crystalline silicates, which process yields a stable catalyst having a high selectivity and a long life.

According to the invention this object is achieved by making the silicate pores inaccessible to a deactivating agent and by subsequently contacting the silicate with the deactivating agent. The silicate pores are made inaccessible to the deactivating agent by saturating the pore volume of the silicate with an organic compound that does not form a solution or mixture with the deactivating agent.

BRIEF DESCRIPTION OF THE DRAWINGS

FIG. 1 schematically depicts the deactivation of a zeolite by cation exchange wherein a proton on the zeolite is exchanged for a sodium ion.

FIG. 2 schematically depicts the deactivation of a boralite by cation exchange wherein a proton on the zeolite is exchanged for a sodium ion.

FIG. 3 schematically illustrates the process according to this invention.

DETAILED DISCUSSION

The organic compound used to saturate the pore volume of the silicate may be any such compound that does not form a solution or a mixture with the deactivating agent or deactivating agent solution, and which can fill the pores of the silicate material by capillary adsorption or capillary saturation.

Suitable organic compounds are apolar organic solvents such as hydrocarbon solvents, in particular aliphatic, aromatic or alkylaromatic hydrocarbons, halogenated hydrocarbon solvents, in particular aliphatic, aromatic or alkylaromatic halogenated hydrocarbons, and etheric solvents, in particular aliphatic ethers. Preferred organic compounds are aliphatic hydrocarbons, such as in particular pentane and hexane, aromatic hydrocarbons such as in particular benzene, and alkylaromatic hydrocarbons such as in particular toluene and xylenes. In the case of silicate materials having particularly small pore sizes (i.e. pores smaller than about 5 Å) the use of linear aliphatic hydrocarbons, most preferably normal alkanes such as n. pentane and n. hexane is recommended.

Suitable deactivating agents are solutions of alkali metal salts in a polar solvent. A very suitable polar solvent is water. Any one of the group 1 A metals can be used in accordance with this invention but the best deactivating results are obtained with lithium, sodium and potassium salts, whereby the sodium salts are mostly prefered. Any soluble salt of said metals can be used, such as in particular halides, nitrates, sulfates and acetates. Halides such as in particular chlorides are very convenient as they are easily available, but salts with anions that can be eliminated merely by heating, such as nitrates or acetates, may be prefered in cases where anion-residues would be undesirable. A very suitable deactivating agent is in particular sodium chloride (NaCl) which is very easily available and cheap.

The concentration of the deactivating solutions should appropriately be from $10^{-3}$ to 5 moles pro liter, preferably from 0.1 to 1 mole pro liter. The process of filling the pore volume of the zeolite or boralite with organic compound can be carried out according to any method known per se. By way of example the silicate material may be made to adsorb the organic compound from a vapour atmosphere until saturation of the pore volume by capillary condensation, or the silicate material, in powder form may be impregnated dropwise with organic compound just until the powder apparently begins to stick together, or the silicate material may be impregnated with an excess of organic compound and drained.

Deactivation of the external surface of the zeolite or boralite is performed by contacting the silicate material with the deactivating agent at a temperature of between 0° and 200° C., for at least half an hour. The contacting of the silicate material with the deactivating agent can be carried out by methods which are also known per se, either in a static way or in a dynamic way.

By way of example the silicate material, the internal pores of which have been filled with organic compound, may be covered with or suspended and agitated in a solution of the deactivating agent for half one hour to about 5 hours, either at atmospheric pressure at a temperature below the boiling point of the solution, or in an autoclave at a temperature up to 200° C.

By filling the pore volume of the zeolite or boralite such that the pore interiors are not accessible to the deactivating agent, selective deactivation of only the external surface is effected.

The (selective) deactivation occurs by a cation exchange mechanism wherein active protons (H+) are exchanged for relatively inactive alkali metal cations, the deactivation mechanism being illustrated by FIGS. 1 and 2, respectively, for a zeolite and a boralite. As both figures show, cations (Na+) from the alkali metal salt exchange with and replace protons (H+) associated with the zeolite or boralite and thereby cause deactivation.

In particular, FIG. 3 illustrates the process of this invention wherein active sites within pores are temporarily masked while active sites on the surface are deactivated. As shown schematically at I, a zeolite or boralite has surface (proton) active sites (two such being shown) near the entrance to the pores, and also active sites (one shown) in the pores themselves. By saturating the silicate with an organic compound (e.g. toluene), as at II, the pore is shown as by the crosshatching to be filled and the active site therein to be masked. The silicate is then exposed to a salt solution which exchanges inactive cations (Na+, for illustration) for protons, thus deactivating the surface active sites. The silicate may then be heated, expelling the organic compound from the pores and yielding a catalyst as shown at IV which has been selectively deactivated only on its external surfaces.

The invention also relates to a crystalline silicate having external surface catalytic properties which differ from those of the pore surface, the silicate being characterized in that at least a portion of the catalytically active sites on the external surface has been replaced by catalytically inactive alkali metal sites. The catalytically active (H+) sites on the external surface of the silicate are, by the process of this invention, at least partly replaced by catalytically inactive alkali metal sites.

The invention will further be elucidated and described by means of examples without, however, being limited to the modes of realization described here.

EXAMPLE I—Application, as catalyst, of a zeolite treated according to the present invention a. Preparation of a HZSM 5—zeolite in accordance with U.S. Pat. No. 3,702,886.

11.5 grams of $SiO_2$ were heated to 100° C. in 42.3 ml of 2.2N $(CH_3CH_2CH_2)_4NOH$. A mixture of 1.45 grams of sodium aluminate (44.5 w.% $Al_2O_3$, 30.1 w.% $Na_2O$, 25.4 w.% $H_2O$) dissolved in 26.9 ml. water was then added, together with 0.035 gram of aluminium turnings dissolved in 10.5 ml. of 2.2.N $(CH_3CH_2CH_2)_4NOH$. The mixture was heated for 8 days to 150° C. in an autoclave. The resultant solid product was filtered and washed, and calcined for 16 hours under air at a temperature of 500° C.

b. Deactivation of the external surface of zeolite, in accordance with the invention 5 g. ZSM.5 zeolite in acid form, as obtained in example 1a in hereabove were impregnated dropwise with toluene, until the zeolite particles tended to stick together. After that the zeolite was suspended and agitated for one hour in 100 ml. of a 0.2M NaCl solution in water, at room temperature. The zeolite was then air dried in an oven for 16 hours at 120° C. and for 16 hours at 500° C. The pores were now entirely free of toluene.

c. application as catalyst of a modified zeolite according to example 1b.

4 grams of the modified zeolite as obtained in according to example 1b hereabove were diluted with 36 grams of Aerosil OX-50 (Registered Trade Mark for high purity amorphous silica having a specific surface area of 50 m²/g, marketed by Degussa). This catalyst sample was introduced in a small fixed bed tubular reactor (diameter 2.5 cm, length 25 cm). The catalyst was heated to 600° C. and purged with nitrogen. A feed of a butylene 1/nitrogen mixture in a molar ratio of 1 was then led over the catalyst at a temperature of 600° C., at a space velocity as given by the following formula $$WHSV = \frac{\text{feed butylene}}{\text{quantity of active catalyst}} \quad \frac{\text{g/hour}}{\text{g}}$$

of 1.4 hour$^{-1}$.

The conversion of the feed butylene continued to be more than 90% for 30 hours. The selectivity to aromatic compounds as calculated by the following formula $$\text{selectivity} = \frac{\text{formed aromatic compounds}}{\text{converted feed butylene}} \quad \frac{g}{g},$$

in the same span of time, only fell from 48% to 30%.

d. Comparison—Application, as catalyst, of an unmodified zeolite according to example 1a 10 parts by weight of the product obtained according to example 1a hereabove were diluted with 90 parts by weight of Aerosil OX-50 (Registered Trade Mark of Degussa, as previously noted) and used as catalyst for the conversion of butylene-1 as described in example 1c. The conversion fell to 93% within 30 hours. In the same span of time the selectivity for the conversion of butylene-1 to aromatic compounds fell from 44% to 13%.

Example II—Application of a boralite, treated according to the invention, as catalyst for the rearrangement of cyclohexanone oxime to ε-caprolactam a. Preparation of a boralite in accordance with U.S. Pat. No. 4,269,813

0.25 g. of $H_3BO_3$ and 1.6 g. of NaOH were dissolved in 60 ml. of distilled water. Then 9.4 g. of $(CH_3CH_2CH_2)_4NOH$ were added. Finally 12.7 g of a 30 wt.% silicasol (stabilized with sodium) were added. The mixture was heated for 7 days at 165° C. in an autoclave. The resultant solid product was filtered and washed, and calcined for 16 hours under air at a temperature of 500° C.

b. 4 g. boralite prepared according to example 2a hereabove was treated as described in example 1b. The thus obtained catalyst sample was introduced in a fixed bed tubular microreactor and a gas mixture of cyclohexanone oxime, toluene. $CO_2$ and water in a molar ratio of 1:3:7:1, respectively, was passed over the boralite treated in this manner at a temperature of 340° C.

The space velocity, as given by the following formula:

$$WHSV = \frac{\text{feed cyclohexanoneoxime}}{\text{quantity active catalyst}} \quad \frac{g/h}{g}$$

was 0.8 hour $^{-1}$.

The conversion of the cyclohexanoneoxime and the selectivity to ε-caprolactam as functions of time are shown in the following table.

| t (hours) | 1 | 2 | 3 | 4 | 5 | 15 |
|---|---|---|---|---|---|---|
| conversion (%) | 100 | 100 | 100 | 100 | 100 | 100 |
| selectivity to ε-caprolactam | 58 | 58 | 58 | 58 | 58 | 58 |

2c. Comparative example—Application of the unmodified boralite obtained according to example 2a as catalyst for the rearrangement of cyclohexanoneoxime to ε-caprolactam The catalyst obtained according to example 2a hereabove was used for the rearrangement of cyclohexanone-oxime to ε-caprolactam under the circumstance described in example II.

The result is shown in the table below.

| t (hours) | 1 | 2 | 3 | 4 | 5 |
|---|---|---|---|---|---|
| conversion (%) | 100 | 99.4 | 98.2 | 96.1 | 93.4 |
| selectivity to ε-caprolactam | 58 | 58 | 58 | 58 | 58 |

Catalysts that have been deactivated in accordance with the known art, involving blocking or poisoning of the active sites on the external surfaces of the silicate materials appear to be less stable at high temperatures than catalysts that have been deactivated in accordance with the invention by replacement of the external active sites by inactive alkaline metals.

What is claimed is:

1. A process for deactivating catalytically active sites on the external surfaces of a catalyst selected from the group consisting of porous crystalline aluminosilicates and porous crystalline borosilicates, consisting essentially in:
   a. contacting said catalyst with an organic compound which substantially fills the pores of said catalyst, thereby masking active sites in the interior of said pores;
   b. contacting the pore-filled catalyst of step (a) with a deactivating agent solution containing an alkali metal salt such that active sites on the external surface of said catalyst are deactivated; and
   c. expelling said organic compound from said pores.

2. The process of claim 1 wherein said organic compound is substantially immiscible with and substantially insoluble in said deactivating agent.

3. The process of claim 1 wherein said organic compound is an aromatic or an alkylaromatic hydrocarbon.

4. The process of claim 3 wherein said hydrocarbon is toluene.

5. The process of claim 1 wherein said deactivating agent is a solution of an alkali metal salt in water.

6. The process of claim 5 wherein said alkali metal salt is a sodium salt.

7. The process of claim 1 wherein said catalyst is contacted with said deactivating agent at a temperature between about 0° C. and about 200° C.

8. The process of claim 1 wherein said catalyst is contacted with said deactivating agent for at least about 30 minutes.

9. The selectively deactivated catalyst obtained by the process of claim 1.

* * * * *

UNITED STATES PATENT AND TRADEMARK OFFICE
CERTIFICATE OF CORRECTION

PATENT NO. : 4,472,516

DATED : September 18, 1984

INVENTOR(S) : Petrus M.G. Frenken

It is certified that error appears in the above-identified patent and that said Letters Patent is hereby corrected as shown below:

Column 3, in each of lines 18 and 23, "prefered" should read --preferred--.

Column 4, line 41, "2.2.N" should read --2.2 N--.

In the table at the bottom of column 5, the text from the top of column 6 should be placed under the text at the bottom of column 5 at line 65. Thereafter, the first four lines at the top of column 6 may be deleted.

Signed and Sealed this

Seventh Day of May 1985

[SEAL]

Attest:

DONALD J. QUIGG

Attesting Officer     Acting Commissioner of Patents and Trademarks